(12) United States Patent
Edelman et al.

(10) Patent No.: US 10,299,915 B2
(45) Date of Patent: May 28, 2019

(54) SYNTHETIC HEART VALVES COMPOSED OF ZWITTERIONIC POLYMERS

(71) Applicant: Boston Scientific SciMed, Inc., Maple Grove, MN (US)

(72) Inventors: Peter G. Edelman, Maple Grove, MN (US); Mark W. Boden, Harrisville, RI (US); Joseph Thomas Delaney, Jr., Minneapolis, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 398 days.

(21) Appl. No.: 15/082,293

(22) Filed: Mar. 28, 2016

(65) Prior Publication Data

US 2016/0296322 A1 Oct. 13, 2016

Related U.S. Application Data

(60) Provisional application No. 62/145,385, filed on Apr. 9, 2015.

(51) Int. Cl.
| | |
|---|---|
| *A61F 2/24* | (2006.01) |
| *A61L 27/00* | (2006.01) |
| *A61L 27/14* | (2006.01) |
| *A61F 2/00* | (2006.01) |

(52) U.S. Cl.
CPC ............ *A61F 2/2412* (2013.01); *A61L 27/00* (2013.01); *A61L 27/14* (2013.01); *A61F 2002/009* (2013.01); *A61F 2310/00389* (2013.01)

(58) Field of Classification Search
None
See application file for complete search history.

(56) References Cited

U.S. PATENT DOCUMENTS

| | | |
|---|---|---|
| 4,016,714 A | 4/1977 | Crandall |
| 4,340,091 A | 7/1982 | Davis et al. |
| 4,753,652 A | 6/1988 | Langer et al. |
| 5,296,292 A | 3/1994 | Butters |
| 5,688,597 A | 11/1997 | Kohno |
| 5,740,051 A | 4/1998 | Sanders, Jr. et al. |
| 6,165,215 A | 12/2000 | Rottenberg et al. |

(Continued)

FOREIGN PATENT DOCUMENTS

| | | |
|---|---|---|
| CN | 1449266 | 10/2003 |
| JP | H0654868 | 3/1994 |

(Continued)

OTHER PUBLICATIONS

Aksoy, Ayse E. et al., "Surface Modification of Polyurethanes with Covalent Immobilization of Heparin," Macromolecular Symposia, vol. 269, Issue 1, pp. 145-153, Aug. 2008 (9 pages).

(Continued)

*Primary Examiner* — Kevin M Bernatz
(74) *Attorney, Agent, or Firm* — Pauly, DeVries Smith & Deffner LLC (57) ABSTRACT

A prosthetic heart valve includes a plurality of synthetic polymeric leaflets. Each leaflet has a base polymer and a polymer coating at least partially disposed over the base polymer, wherein the polymer coating includes polymerized units of a monomer comprising a zwitterionic group when the polymer coating is exposed to an aqueous environment at a pH of about 7.4.

16 Claims, 4 Drawing Sheets

(56) References Cited

U.S. PATENT DOCUMENTS

| | | | |
|---|---|---|---|
| 6,726,715 B2 | 4/2004 | Sutherland | |
| 6,953,332 B1 | 10/2005 | Kurk et al. | |
| 7,335,264 B2 | 2/2008 | Austin et al. | |
| 7,517,353 B2 | 4/2009 | Weber | |
| 7,521,296 B2 | 4/2009 | Wood et al. | |
| 7,615,335 B2 | 11/2009 | Shelnut et al. | |
| 7,786,670 B2 | 8/2010 | Veres et al. | |
| 7,988,900 B2 | 8/2011 | Beith et al. | |
| 8,324,290 B2 | 12/2012 | Desai et al. | |
| 8,361,144 B2* | 1/2013 | Fish | A61F 2/0095 |
| | | | 435/1.1 |
| 8,590,747 B2 | 11/2013 | Keller et al. | |
| 8,845,580 B2 | 9/2014 | Gellman et al. | |
| 8,864,816 B2 | 10/2014 | Flanagan et al. | |
| 9,056,006 B2* | 6/2015 | Edelman | A61F 2/2412 |
| 9,074,318 B2 | 7/2015 | Chou et al. | |
| 9,255,929 B2* | 2/2016 | Jiang | G01N 33/6845 |
| 9,554,900 B2 | 1/2017 | Bruchman et al. | |
| 9,737,400 B2* | 8/2017 | Fish | A61F 2/2415 |
| 9,814,572 B2 | 11/2017 | Edelman et al. | |
| 2001/0025196 A1 | 9/2001 | Chinn et al. | |
| 2002/0082689 A1 | 6/2002 | Chinn et al. | |
| 2003/0055496 A1 | 3/2003 | Cai et al. | |
| 2003/0078652 A1 | 4/2003 | Sutherland et al. | |
| 2003/0097175 A1* | 5/2003 | O'Connor | A61F 2/2412 |
| | | | 623/2.17 |
| 2003/0171802 A1 | 9/2003 | Wilder et al. | |
| 2003/0183982 A1 | 10/2003 | Jansen et al. | |
| 2004/0015233 A1 | 1/2004 | Jansen et al. | |
| 2004/0022939 A1 | 2/2004 | Kim et al. | |
| 2005/0228486 A1 | 10/2005 | Flagle et al. | |
| 2006/0190074 A1 | 8/2006 | Hill et al. | |
| 2007/0118210 A1* | 5/2007 | Pinchuk | A61F 2/2412 |
| | | | 623/1.26 |
| 2007/0144124 A1 | 6/2007 | Schewe et al. | |
| 2007/0232169 A1 | 10/2007 | Strickler et al. | |
| 2007/0254005 A1* | 11/2007 | Pathak | A61K 35/12 |
| | | | 424/423 |
| 2008/0045420 A1 | 2/2008 | Karagianni et al. | |
| 2009/0041978 A1 | 2/2009 | Sogard et al. | |
| 2009/0054969 A1 | 2/2009 | Salahieh et al. | |
| 2009/0117334 A1 | 5/2009 | Sogard et al. | |
| 2009/0149673 A1* | 6/2009 | Zhang | C07C 229/26 |
| | | | 562/553 |
| 2009/0155335 A1* | 6/2009 | O'Shaughnessey | A61L 15/46 |
| | | | 424/423 |
| 2009/0324679 A1* | 12/2009 | Ippoliti | A61L 31/06 |
| | | | 424/423 |
| 2010/0023104 A1 | 1/2010 | Desai et al. | |
| 2010/0179298 A1 | 7/2010 | Faust et al. | |
| 2010/0249922 A1 | 9/2010 | Li et al. | |
| 2011/0022160 A1 | 1/2011 | Flanagan et al. | |
| 2011/0208299 A1 | 8/2011 | Marissen et al. | |
| 2011/0305898 A1* | 12/2011 | Zhang | A61L 27/34 |
| | | | 428/336 |
| 2012/0258313 A1* | 10/2012 | Wen | C09D 131/00 |
| | | | 428/412 |
| 2013/0150957 A1 | 6/2013 | Weber et al. | |
| 2013/0211508 A1 | 8/2013 | Lane et al. | |
| 2013/0274874 A1 | 10/2013 | Hammer et al. | |
| 2014/0005771 A1 | 1/2014 | Braido et al. | |
| 2014/0005772 A1 | 1/2014 | Edelman et al. | |
| 2014/0018440 A1 | 1/2014 | Boden et al. | |
| 2014/0088716 A1 | 3/2014 | Zubok et al. | |
| 2014/0163671 A1 | 6/2014 | Bruchman et al. | |
| 2014/0180402 A1 | 6/2014 | Bruchman et al. | |
| 2014/0322512 A1 | 10/2014 | Pham et al. | |
| 2015/0182332 A1 | 7/2015 | Edelman et al. | |
| 2015/0265392 A1* | 9/2015 | Flanagan | A61F 2/04 |
| | | | 623/23.65 |
| 2016/0296323 A1* | 10/2016 | Wulfman | A61F 2/2412 |
| 2016/0296325 A1 | 10/2016 | Edelman | |
| 2017/0000610 A1 | 1/2017 | Eppihimer et al. | |
| 2017/0014227 A1 | 1/2017 | Boden et al. | |
| 2017/0071729 A1 | 3/2017 | Wrobel | |
| 2017/0156854 A1* | 6/2017 | Hammer | A61F 2/24 |
| 2017/0231758 A1* | 8/2017 | Bruchman | A61F 2/2415 |
| | | | 156/331.7 |
| 2017/0266350 A1* | 9/2017 | Jiang | A61K 9/0024 |
| 2017/0333185 A1 | 11/2017 | Weber et al. | |
| 2018/0049869 A1 | 2/2018 | Edelman et al. | |

FOREIGN PATENT DOCUMENTS

| | | | |
|---|---|---|---|
| WO | 0224119 | 3/2002 | |
| WO | 02074201 | 9/2002 | |
| WO | 2006000763 | 1/2006 | |
| WO | WO-2006000763 A2 * | 1/2006 | A61L 27/40 |
| WO | 2008097592 | 8/2008 | |
| WO | 2009038761 | 3/2009 | |
| WO | 2010020660 | 2/2010 | |
| WO | 2010048281 | 4/2010 | |
| WO | 2014008207 | 1/2014 | |
| WO | WO-2014008207 A1 * | 1/2014 | A61F 2/2412 |
| WO | 2014143866 | 8/2014 | |
| WO | 2014149319 | 9/2014 | |
| WO | 2016025945 | 2/2016 | |
| WO | 2016164197 | 10/2016 | |
| WO | 2016164209 | 10/2016 | |
| WO | 2017004035 | 1/2017 | |
| WO | 2017011392 | 1/2017 | |
| WO | 2017048575 | 3/2017 | |
| WO | 2017200920 | 11/2017 | |

OTHER PUBLICATIONS

Alferiev, Ivan et al., "Prevention of polyurethane valve cusp calcification with covalently attached bisphosphonate diethylamino moieties," J Biomed Mater Res 66A: 385-395, 2003 (11 pages).

Athappan, Ganesh et al., "Influence of Transcatheter Aortic Valve Replacement Strategy and Valve Design on Stroke After Transcatheter Aortic Valve Replacement: A Meta-Analysis and Systematic Review of Literature," J Am Coll Cardiol. 2014;63(20):2101-2110 (10 pages).

Barkoula, Nektaria-Marianthi et al., "Processing of Single Polymer Composites Using the Concept of Constrained Fibers," Polymer Composites, 2005, 26: p. 114-120 (7 pages).

Bastiaansen, Cees W. et al., "Melting Behavior of Gelspun-Drawn Polyolefins," Makromol. Chem., Macromol. Symp., 1989. 28: p. 73-84 (12 pages).

Bates, Frank S. et al., "Multiblock Polymers: Panacea or Pandora's Box?," Science, 2012, 336:434-440 (7 pages).

Bernacca, Gillian M. et al., "Mechanical and morphological study of biostable polyurethane heart valve leaflets explanted from sheep," J Biomed Mater Res 61:138-145, 2002 (8 pages).

Bhattacharyya, D. et al., "Polyamide 6 single polymer composites," eXPRESS Polym. Lett., 2009. 3(8): p. 525-532 (8 pages).

Charles, Lyndon F. et al., "Self-reinforced composites of hydroxyapatite-coated PLLA fibers: fabrication and mechanical characterization," J. Mech. Behav. Biomed. Mater., 2013. 17: p. 269-277 (9 pages).

Claiborne, Thomas E. et al., "In Vitro Evaluation of a Novel Hemodynamically Optimized Trileaflet Polymeric Prosthetic Heart Valve," Journal of Biomechanical Engineering 2013, vol. 135 (8 pages).

De Yoreo, James J. et al., "Principles of Crystal Nucleation and Growth," Biomineralization, Mineral Soc. Am., Washington, DC, 2003, pp. 57-93 (37 pages).

Dencheva, Nadya et al., "Structure-properties relationship in single polymer composites based on polyamide 6 prepared by in-mold anionic polymerization," J. Mater. Sci., 2013. 48(20): p. 7260-7273 (14 pages).

Duhovic, Miro P. et al., "Polyamide 66 polymorphic single polymer composites," Open Macromol. J., 2009. 3: p. 37-40. (4 pages).

Fakirov, Stoyko "Nano- and Microfibrillar Single-Polymer Composites: A Review," Macromol. Mater. Eng., 2013. 298(1): p. 9-32 (24 pages).

Feng, Yakai et al., "Surface modification of polycarbonate urethane by covalent linkage of heparin with a PEG spacer," Transactions of Tianjin University, Feb. 2013, vol. 19, Issue 1, pp. 58-65 (8 pages).

(56) References Cited

OTHER PUBLICATIONS

File History for U.S. Appl. No. 13/932,968, (297 pages).
File History for U.S. Appl. No. 14/656,044, (169 pages).
"First Office Action," for Chinese Patent Application No. 201380044842.0 dated Dec. 18, 2015 (15 pages) with English Translation.
Généreux, Philippe et al., "Vascular Complications After Transcatheter Aortic Valve Replacement: Insights from the PARTNER Trial," J Am Coll Cardiol. 2012;60(12):1043-1052 (10 pages).
"Glycosaminoglycan," Wikipedia, posted on or before Oct. 16, 2004, retrieved Feb. 13, 2014, http://en.wikipedia.org/wiki/Glycosaminoglycan, 6 pages.
Gong, Ying et al., "Polyamide single polymer composites prepared via in situ anionic polymerization of ε-caprolactam," Composites, Part A, 2010. 41A(8): p. 1006-1011 (6 pages).
Gong, Ying et al., "Single polymer composites by partially melting recycled polyamide 6 fibers: preparation and characterization," J. Appl. Polym. Sci., 2010. 118(6): p. 3357-3363 (7 pages).
Goyal, R. K. et al., "High performance polymer composites on PEEK reinforced with aluminum oxide," J. Appl. Polym. Sci., 2006. 100(6): p. 4623-4631 (9 pages).
Han, Dong K. et al., "In vivo biostability and calcification-resistance of surface-modified PU-PEO-SO3," Journal of Biomedical Materials Research, vol. 27, 1063-1073, 1993 (11 pages).
Hine, P.J. et al., "High stiffness and high impact strength polymer composites by hot compaction of oriented fibers and tapes.," in Mechanical Properties of Polymers Based on Nanostructure and Morphology, CRC Press, 2005 (45 pages).
Hine, P.J. et al., "Hot compaction of woven nylon 6,6 multifilaments," J. Appl. Polym. Sci., 2006. 101(2): p. 991-997 (7 pages).
Hine, P.J. et al., "Hot Compaction of Woven Poly(ethylene terephthalate) Multifilaments," J. Appl. Polym. Sci., 2004. 91(4): p. 2223-2233 (11 pages).
Hine, P.J. et al., "Hybrid carbon fibre/nylon 12 single polymer composites," Composites Part A: Applied Science and Manufacturing 65 (2014) (17 pages).
"International Preliminary Report on Patentability," For International Application No. PCT/US2013/048976 dated Jan. 6, 2015 (9 pages).
"International Search Report & Written Opinion," for International Application No. PCT/US2013/048976 dated Nov. 19, 2013 (20 pages).
Jiang, Shaoyi et al., "Ultralow-Fouling, Functionalizable, and Hydrolyzable Zwitterionic Materials and Their Derivatives for Biological Applications," Adv Mater. Mar. 5, 2010;22(9):920-32 (13 pages).
Kaflon-Cohen, Estelle et al., "Microstructure and nematic transition in thermotropic liquid crystalline fibers and their single polymer composites," Polym. Adv. Technol., 2007. 18(9): p. 771-779 (9 pages).
Kang, Jungmee et al., "Polyisobutylene-Based Polyurethanes with Unprecedented Properties and How They Came About," Journal of Polymer Science Part A: Polymer Chemistry, 2011. 49(18): p. 3891-3904 (14 pages).
Khondker, O.A. et al., "Fabrication and mechanical properties of aramid/nylon plain knitted composites," Composites Part A: Applied Science and Manufacturing, 2004. 35(10): p. 1195-1205 (11 pages).
Kim, Nam K. et al., "Nanofibrillar Poly(vinylidene fluoride): Preparation and Functional Properties," Int. J. Polym. Mater. Polym. Biomater., 2014. 63(1): p. 23-32 (10 pages).
Kim, Nam K. et al., "Polymer-Polymer and Single Polymer Composites Involving Nanofibrillar Poly(vinylidene Fluoride): Manufacturing and Mechanical Properties," J. Macromol. Sci., Part B: Phys., 2014. 53(7): p. 1168-1181 (14 pages).
"Liquid-Crystal Polymer," Wikipedia, the Free Encyclopedia <http://en/wikipedia.org/wiki/Liquid-crystal_polymer>, retrieved Jun. 2, 2016 (3 pages).
Liu, et al., "Effect of fiber orientation on the stress distribution within a leaflet of a polymer composite heart valve in the closed position," J of Biomedichanics, 2007, 40:1099-1106 (8 pages).

Maity, J. et al., "Homocomposites of chopped fluorinated polyethylene fiber with low-density polyethylene matrix," Mater. Sci. Eng., A, 2008. A479(1-2): p. 125-135 (11 pages).
Matabola, K. P. et al., "Single polymer composites: a review," Journal of Materials Science, 2009. 44(23): p. 6213-6222 (10 pages).
Medeiros Araujo, Thiago et al., "Liquid crystalline single-polymer short-fibers composites," Composite Interfaces, 2013. 20(4): p. 287-298 (12 pages).
Ohri, Rachit et al., "Hyaluronic acid grafting mitigates calcification of glutaraldehyde-fixed bovine pericardium," J Biomed Mater Res 70A: 328-334, 2004 (7 pages).
Schneider, Tobias et al., "Influence of fiber orientation in electrospun polymer scaffolds on viability, adhesion and differentiation of articular chondrocytes," Clinical Hemorheology and Microcirculation 52 (2012) 325-336 (13 pages).
Sun, Xiaoli et al., "β and β Interfacial Structures of the iPP/PET Matrix/Fiber Systems," Macromolecules, 2007. 40(23): p. 8244-8249 (6 pages).
Vick, Linda W. et al., "Hot compaction and consolidation of polycarbonate powder," Polym. Eng. Sci., 1998. 38(11): p. 1824-1837 (14 pages).
Wang, Qiang et al., "A novel small animal model for biocompatibility assessment of polymeric materials for use in prosthetic heart valves," J Biomed Mater Res 93A: 442-453, 2010 (12 pages).
Wang, Qiang et al., "In-Vivo Assessment of a Novel Polymer (SIBS) Trileaflet Heart Valve," J Heart Valve Dis, Jul. 2010, 19(4):499-505 (7 pages).
Ward, I.M. et al., "Developments in oriented polymers," Plastics, Rubber and Composites, 2004. 33(5): p. 189-194 (6 pages).
Ward, I.M. et al., "Novel composites by hot compaction of fibers," Polym. Eng. Sci., 1997. 37(11): p. 1809-1814 (6 pages).
Wheatley, et al., "Polyurethane: material for the next generation of heart valve prostheses?," Eur J Cardio-Thoracic Surg, 2000, 17:440-448 (11 pages).
Yang, Mingjing et al., "Assessing the Resistance to Calcification of Polyurethane Membranes Used in the Manufacture of Ventricles for a Totally Implantable Artificial Heart," J Biomed Mater Res (Appl Biomater) 48: 648-659, 1999 (12 pages).
Yao, Jian et al., "High Strength and High Modulus Electrospun Nanofibers," Fibers 2014; 2:158-187 (30 pages).
Yeh, Shiou-Bang et al., "Modification of Silicone Elastomer with Zwitterionic Silane for Durable Antifouling Properties," Langmuir 2014, 30, 11386-11393 (8 pages).
Zhang, Baoyan et al., "Studies of Novel Segmented Copolyether Polyurethanes," Eur. Polym. J., vol. 34, No. 3-4, pp. 571-575 (1998) (5 pages).
Zhang, Zhiping et al., "Effect of Crosslinking and Grafting by 60Co-γ-ray Irradiation on Carbon Black/Polyethylene Switching Materials and Fluoride Resin System in self-regulating Heating Cables," JAERI-Conf, 2000. 2000-001(JCBSRC '99, the 8th Japan-China Bilateral Symposium on Radiation Chemistry, 1999): p. 202-210 (9 pages).
Zhao, Zeng Hua et al., "Research development of single polymer composite preparation," Gongcheng Suliao Yingyong, 2010. 38(2): p. 81-84, with machine translation (11 pages).
"Decision of Final Rejection," for China Patent Application No. 201380044842.0, dated Apr. 7, 2017 (18 pages) with Summary.
"Non-Final Office Action," for U.S. Appl. No. 14/656,044 dated Mar. 17, 2017 (34 pages).
"Response to Non-Final Office Action," for U.S. Appl. No. 14/656,044 dated Mar. 17, 2017 and filed with the USPTO Jun. 8, 2017 (11 pages).
Berkland, Cory et al., "Controlling surface nano-structure using flow-limited field-injection electrostatic spraying (FFESS) of poly(D,L-lactide-co-glycolide)," Biomaterials (2004) 25: 5649-5658 (10 pages).
Fabreguette, et al., "X-ray mirrors on flexible polymer substrates fabricated by atomic layer deposition," Thin Solid Films 515: 7177-7180 (2007), 5 pages.
Fabreguette, Francois H. et al., "Ultrahigh x-ray reflectivity from W/Al2O3 multilayers fabricated using atomic layer deposition," Applied Physics Letters 88: 013166 (2006), 3 pages.

(56) References Cited

OTHER PUBLICATIONS

"Final Office Action," for U.S. Appl. No. 15/193,794 dated May 23, 2018 (12 pages).
George, "Final Report—Fabrication of Nanolaminates with Ultrathin Nanolayers Using Atomic Layer Deposition: Nucleation & Growth Issues," AFOSR Grant No. FA9550-01-1-0075 Feb. 2009 (36 pages).
Groner, M. D. et al., "Gas Diffusion Barriers on Polymers Using Al2O3 Atomic Layer Deposition," Applied Physics Letters 88, 051907, 2006 (3 pages).
Hass, D. D. et al., "Ractive vapor deposition of metal oxide coatings," Surface and Coatings Technology 146-147 (2001) 85-93.
"International Preliminary Report on Patentability," for PCT Application No. PCT/US2016/024614 dated Oct. 19, 2017 (7 pages).
"International Preliminary Report on Patentability," for PCT Application No. PCT/US2016/024753 dated Oct. 19, 2017 (7 pages).
"International Preliminary Report on Patentability," for PCT Application No. PCT/US2016/039808 dated Jan. 11, 2018 (8 pages).
"International Preliminary Report on Patentability," for PCT Application No. PCT/US2016/041757 dated Jan. 25, 2018 (8 pages).
"International Preliminary Report on Patentability," for PCT Application No. PCT/US2016/050691 dated Mar. 29, 2018 (9 pages).
"International Search Report and Written Opinion," for PCT Application No. PCT/US2017/032656 dated Jul. 21, 2017 (16 pages).
Jen, Shih-Hui et al., "Critical tensile and compressive strains for cracking of Al2O3 films grown by atomic layer deposition," Journal of Applied Physics 109, 084305 (2011), 11 pages.
Jen, Shih-Hui et al., "Critical tensile strain and water vapor transmission rate for nanolaminate films grown using Al2O3 atomic layer deposition and alucone molecular layer deposition," Applied Physics Letters 101, 234103 (2012), 3 pages.
Mach, H. et al., "Highly Reactive Polyisobutene as a Component of a New Generation of Lubricant and Fuel Additives," Lubrication Science 1999, 11 (2), 175-185.
"Non-Final Office Action," for U.S. Appl. No. 15/082,239 dated May 16, 2018 (34 pages).
"Non-Final Office Action," for U.S. Appl. No. 15/193,794 dated Mar. 14, 2018 (14 pages).
"Non-Final Office Action," for U.S. Appl. No. 15/193,794 dated Nov. 6, 2017 (32 pages).
"Non-Final Office Action," for U.S. Appl. No. 15/257,211 dated Apr. 10, 2018 (39 pages).
Raghavan, R. et al., "Nanocrystalline-to-amorphous transition in nanolaminates grown by low temperature atomic layer deposition and related mechanical properties," Applied Physics Letters 100, 191912 (2012), 9 pages.
"Response to Communication Pursuant to Rules 161(1) and 162 EPC," for European Patent Application No. 13739321.1 filed with the EPO Jul. 7, 2015 (20 pages).
"Response to Communication Pursuant to Rules 161(1) and 162 EPC," for European Patent Application No. 16715218.0 filed May 25, 2018, 13 pages.
"Response to Communication Pursuant to Rules 161(1) and 162 EPC," for European Patent Application No. 16715724.7 filed May 25, 2018, (7 pages).
"Response to Non-Final Office Action," for U.S. Appl. No. 15/193,794 dated Mar. 14, 2018 and filed with the USPTO Apr. 16, 2018 (8 pages).
"Response to Non-Final Office Action," for U.S. Appl. No. 15/193,794, dated Nov. 6, 2017 and filed with the USPTO Feb. 13, 2018 (7 pages).
Rutledge, G.C. et al., "Electrostatic Spinning and Properties of Ultrafine Fibers," National Textile Center Annual Report: Nov. 2001, M01-D22, (10 pages).
Shin, Y. M. et al., "Experimental characterization of electrospinning: the electrically forced jet and instabilities," Polymer 42 (2001) 9955-9967 (13 pages).
Szeghalmi, Adriana et al., "All dielectric hard x-ray mirror by atomic layer deposition," Applied Physics Letters 94, 133111 (2009), 3 pages.

Szilagyi, Imre M. et al., "Review on One-Dimensional Nanostructures Prepared by Electrospinning and Atomic Layer Deposition," INERA Workshop of ISCMP2014, IOP Publishing, Journal of Physics: Conference Series 559, 2014 (13 pages).
"International Search Report and Written Opinion," for PCT Application No. PCT/US2016/041757 dated Oct. 12, 2016 (12 pages).
"International Search Report and Written Opinion," for PCT application No. PCT/US2016/050691 dated Dec. 19, 2016 (14 pages).
Kuang, Jinghao et al., "Universal Surface-initiated Polymerization of Antifouling Zwitterionic Brushes Using a Mussel Mimetic Peptide Initiator," Langmuir. May 8, 2012; 28(18): 7258-7266 (20 pages).
"Response to Communication Pursuant to Article 94(3) EPC," for European Patent Application No. 13739321.1 filed with the EPO Jan. 2, 2017 (37 pages).
"Response to Final Office Action," for U.S. Appl. No. 14/656,044, dated Sep. 9, 2016 and filed with the USPTO Dec. 8, 2016 (9 pages).
"Second Office Action," for Chinese Patent Application No. 201380044842.0, dated Aug. 12, 2016 (16 pages) with summary.
Tu, Qin et al., "Synthesis of Polyethylene Glycol- and Sulfobetaine-Conjugated Zwitterionic Poly(l-lactide) and Assay of its Antifouling Properties," Colloids and Surfaces B; Biointerfaces 102 (2013) 331-340 (10 pages).
Cacciola, G. et al., "A Synthetic Fiber-Reinforced Stentless Heart Valve," Journal of Biomechanics, Jan. 1, 2000, pp. 653-658, XP055284947, Retrieved from the Internet: URL:http://ac.els-cdn.com.
Cacciola, G. et al., "A Three-Dimensional Mechanical Analysis of a Stentless Fibre-Reinforced Aortic Valve Prosthesis," Journal of Biomechanics, Jan. 1, 2000, pp. 521-530, XP055284955, Retrieved from the Internet: URL:http://ac.els-cdn.com.
"Communication Pursuant to Article 94(3) EPC," for European Patent Application No. 13739321.1 dated Sep. 8, 2016 (4 pages).
"Final Office Action," for U.S. Appl. No. 14/656,044 dated Sep. 9, 2016 (17 pages).
Gallocher, "Durability Assessment of Polymer Trileaflet Heart Valves," FIU Electronic Theses and Dissertations, Paper 54, 2007 (237 pages).
"International Search Report and Written Opinion," for PCT/US2016/024614 dated Jul. 12, 2016 (13 pages).
"International Search Report and Written Opinion," for PCT/US2016/024753 dated Jul. 22, 2016 (11 pages).
"International Search Report and Written Opinion," for PCT/US2016/039808 dated Sep. 26, 2016 (11 pages).
Kalejs, et al., "St. Jude Epic Heart Valve Bioprostheses Versus Native Human and Porcine Aortic Valves—Comparison of Mechanical Properties," Interactive Cardiovascular and Thoracic Surgery 8 (2009) 553-557.
Masoumi, et al., "Trilayered Elastomeric Scaffolds for Engineering Heart Valve Leaflets," Biomaterials. Sep. 2014; 35(27):7774-7785.
"Response to Non-Final Office Action," for U.S. Appl. No. 14/656,044, dated May 20, 2016 and filed with the USPTO Aug. 9, 2016 (11 pages).
Vesely, et al., "Micromechanics of the Fibrosa and the Ventricularis in Aortic Valve Leaflets," J Biomech. 1992 25(1):101-113.
Final Office Action for U.S. Appl. No. 15/257,211 dated Jul. 26, 2018 (13 pages).
International Search Report and Written Opinion for PCT Application No. PCT/US2018/028864 dated Jul. 30, 2018 (10 pages).
Madhusha, "Difference between Fluorine and Fluoride," Aug. 9, 2017, PEDIAA.com, pp. 1-8. URL <http://pediaa.com/difference-between-fluorine-and-fluoride/> (8 pages).
Non-Final Office Action for U.S. Appl. No. 15/082,382 dated Sep. 19, 2018 (8 pages).
Non-Final Office Action for U.S. Appl. No. 15/595,176 dated Aug. 27, 2018 (30 pages).
Non-Final Office Action for U.S. Appl. No. 15/797,394 dated Sep. 26, 2018 (39 pages).
Notice of Allowance for U.S. Appl. No. 15/257,211 dated Sep. 24, 2018 (7 pages).
Response to Communication Pursuant to Rules 161(1) and 162 EPC for European Patent Application No. 16736720.0 filed with the EPO Jul. 12, 2018 (12 pages).

(56) References Cited

OTHER PUBLICATIONS

Response to Final Office Action for U.S. Appl. No. 15/193,794, dated May 23, 2018 and filed with the USPTO Jul. 17, 2018 (10 pages).
Response to Final Rejection dated Jul. 26, 2018, for U.S. Appl. No. 15/257,211, submitted via EFS-Web on Aug. 9, 2018.
Response to Non-Final Office Action for U.S. Appl. No. 15/082,239, dated May 16, 2018 and filed with the USPTO Jun. 19, 2018 (13 pages).
Response to Non-Final Office Action for U.S. Appl. No. 15/257,211, dated Apr. 10, 2018 and filed with the USPTO Jun. 18, 2018 (10 pages).

\* cited by examiner

SYNTHETIC HEART VALVES COMPOSED OF ZWITTERIONIC POLYMERS

This application claims the benefit of U.S. Provisional Application No. 62/145,385 filed Apr. 9, 2015, the contents of which are herein incorporated by reference.

TECHNICAL FIELD

This invention relates to medical devices, systems and related methods that include synthetic polymers having zwitterionic pendant groups.

BACKGROUND

Heart function can be significantly impaired when a heart valve is not functioning properly. Potential causes for heart valve malfunction include dilation of an annulus around the valve, ventricular dilation, and a prolapsed or misshapen valve leaflet. When the heart valve is unable to close properly, blood within a heart chamber can leak backwards, which is commonly referred to as regurgitation, through the valve. A defective heart valve may be treated by replacing the diseased valve with a replacement heart valve.

Artificial heart valves made from synthetic materials provide an attractive alternative to prosthetic heart valves. Prosthetic heart valves are constructed of animal tissues, such as bovine pericardium and porcine tissue, which are not durable as some available synthetic materials. Artificial heart valves made of synthetic materials can therefore function over a longer use life as compared to prosthetic heart valves. There are some limitations to using synthetic materials, however, as these materials are more prone to calcification. Heart valve calcification is a condition in which calcium deposits form on the leaflets of a heart valve and cause issues such as valve stenosis, blood flow restriction and possibly valve malfunction.

Differences in polymer structure and surface chemistry among some commonly available polymers, such as polyether urethanes and polycarbonate urethanes, may contribute to synthetic material calcification. New generation polyurethanes with siloxane soft segments have shown better performance but also have limitations. Even thermoplastic elastomers with polyisobutylene midblocks have not been without issues. Other studies have shown that surface modifications can mitigate the degree to which surfaces can become calcified. For example, approaches employing controlled release of bisphosphonates and surface modification using bisphosphonates, sulfate modifications, and glycoseaminoglycans such as hyaluronic acid and heparin, have been employed and evaluated. All these materials and approaches, however, have their limitations in effectiveness and manufacturability. There remains a continuing need for synthetic materials that minimize or prevent calcification such that a prosthetic heart valve can retain functionality throughout the life of a patient.

SUMMARY

Prosthetic heart valves provided herein are adapted to optimize functionality during the life of a patient and to provide anti-calcification properties to synthetic leaflet materials. Prosthetic heart valves provided herein can include leaflets made of synthetic polymers that include zwitterionic pendant groups.

In Example 1, a prosthetic heart valve includes a plurality of synthetic polymeric leaflets. Each leaflet can have a base polymer and a polymer coating at least partially disposed over the base polymer. The prosthetic heart valve can be characterized by the polymer coating including polymerized units of a monomer including a zwitterionic group when the polymer coating is exposed to an aqueous environment, in particular blood, at a pH of about 7.4.

In Example 2, the prosthetic heart valve of example 1, wherein the anion of the zwitterionic group is formed by a carboxylic acid group, a sulfonic acid group, or a phosphoric acid group.

In Example 3, the prosthetic heart valve of example 1 or example 2, wherein the cation of the zwitterionic group is formed by an (cyclo)aliphatic or aromatic amine, an amidine, or a guanidine; or is a quaternary amine.

In Example 4, the prosthetic heart valve of one of examples 1-3, wherein the cation is a quaternary amine.

In Example 5, the prosthetic heart valve of one of examples 1-4, wherein the cation and the anion of the zwitterionic group are part of the same pendant group of the monomer unit.

In Example 6, the prosthetic heart valve of one of examples 1-5, wherein the pendant group has the structure X—(CH2)n-N+R2-(CH2)m-Y or X—(CH2)n-O—P(O—)—(CH2)m-Z, wherein:

X is the point of covalent attachment to the repeat unit of the monomer;

each R is independently selected from C1- to C4-alkyl, in particular methyl;

n and m are each integers between 1 and 8, in particular between 2 and 3;

Y is a anionic group selected from COO—, SO3-, O—SO3-, O—PO3-, and PO3-; and

Z is a cationic group derived from a (cyclo)aliphatic or aromatic amine, an amidine, a guanidine, or a quaternary amine, in particular NR'3+, wherein each R' is independently selected from C1- to C4-alkyl.

In Example 7, the prosthetic heart valve of one of examples 1-6, wherein the monomer including a zwitterionic group is an acrylate, a methacrylate, an acrylamide, or a methacrylamide.

In Example 8, the prosthetic heart valve of one of examples 1-7, wherein the polymer is formed from a monomer having a structure selected from the group consisting of:

Formula 4

In Example 9, the prosthetic heart valve of one of examples 1-8, wherein the base polymer includes an elastic polymer.

In Example 10, the prosthetic heart valve of one of examples 1-9, wherein each leaflet includes a plurality of fibers.

In Example 11, the prosthetic heart valve of examples 1-10, wherein the plurality of fibers are embedded in the base polymer.

In Example 12, the prosthetic heart valve of example 10 or example 11, wherein the plurality of fibers are each oriented in an extending direction and each includes a plurality of undulations, wherein the plurality of undulations of the plurality of fibers are adapted to provide each leaflet with multi-stage elastic properties.

In Example 13, the prosthetic heart valve of one of examples 1-12, wherein the prosthetic heart valve includes an expandable tubular body, wherein the expandable tubular body includes a polymer layer including the same polymer as the base polymer of the plurality of leaflets.

In Example 14, the prosthetic heart valve of one of examples 1-13, wherein the base polymer includes polyisobutylene polyurethanes (PIB-PUR).

In Example 15, a method of forming an artificial heart leaflet includes applying a synthetic polymeric coating to at least one leaflet of an artificial heart valve. The synthetic polymeric coating is formed from one or more monomers, wherein at least one monomer includes a zwitterionic pendant group.

In Example 16, a prosthetic heart valve includes a plurality of synthetic polymeric leaflets. Each leaflet can include a base polymer and a polymer coating disposed over at least a portion of the base polymer. The prosthetic heart valve can be characterized by the polymer coating formed from a monomer including zwitterionic pendant groups.

In Example 17, the prosthetic heart valve of example 16, wherein the anion of the zwitterionic group is formed by a carboxylic acid group, a sulfonic acid group, or a phosphoric acid group.

In Example 18, the prosthetic heart valve of example 16, wherein the cation of the zwitterionic group is formed by an (cyclo)aliphatic or aromatic amine, an amidine, or a guanidine; or is a quaternary amine.

In Example 19, the prosthetic heart valve of example 16, wherein polymer coating consists essentially of polymerized units of monomers each including a zwitterionic group.

In Example 20, the prosthetic heart valve of example 16, wherein the cation is a quaternary amine.

In Example 21, the prosthetic heart valve of example 16, wherein the cation and the anion of the zwitterionic group are part of the same pendant group of the monomer unit.

In Example 22, the prosthetic heart valve of example 16, wherein the cation and the anion of the zwitterionic group are part of the same pendant group of the monomer unit.

In Example 23, the prosthetic heart valve of example 16, wherein the pendant group has the structure X—(CH2)n-N+R2-(CH2)m-Y or X—(CH2)n-O—P(O—)—(CH2)m-Z, wherein:

X is the point of covalent attachment to the repeat unit of the monomer;

each R is independently selected from C1- to C4-alkyl, in particular methyl;

n and m are each integers between 1 and 8, in particular between 2 and 3;

Y is a anionic group selected from COO—, SO3-, O—SO3-, O—PO3-, and PO3-; and Z is a cationic group derived from a (cyclo)aliphatic or aromatic amine, an amidine, a guanidine, or a quaternary amine, in particular NR'3+, wherein each R' is independently selected from C1- to C4-alkyl.

In Example 23, the prosthetic heart valve of example 16, wherein the polymer is formed from one or more monomer species having a structure selected from the group consisting of:

-continued

Formula 4

Formula 5

Formula 6

In Example 24, the prosthetic heart valve of example 16, wherein the monomer including a zwitterionic group is an acrylate, a methacrylate, an acrylamide, or a methacrylamide.

In Example 25, the prosthetic heart valve of example 16, wherein the base polymer includes an elastic polymer.

In Example 26, the prosthetic heart valve of example 16, wherein each leaflet includes a plurality of fibers.

In Example 27, the prosthetic heart valve of example 16, wherein the plurality of fibers are embedded in the base polymer, each fiber being oriented in an extending direction and including a plurality of undulations.

In Example 28, the prosthetic heart valve of example 16, wherein the prosthetic heart valve includes an expandable tubular body, wherein the expandable tubular body includes a polymer layer including the same polymer as the base polymer of the plurality of leaflets.

In Example 29, the prosthetic heart valve of example 16, wherein the base polymer includes polyisobutylene polyurethanes (PIB-PUR).

In Example 30, a prosthetic heart valve includes a plurality of synthetic polymeric leaflets. Each leaflet can include a base polymer and a polymer coating disposed over the base polymer, wherein the polymer coating is formed from one or more monomers including zwitterionic pendant groups and one or more monomer including non-zwitterionic pendent groups.

In Example 31, the prosthetic heart valve of example 30, wherein the polymer coating formed from a monomer including zwitterionic pendant groups having a structure selected from the group consisting of:

Formula 4

Formula 5

Formula 6

In Example 32, a method of forming an artificial heart leaflet includes applying a synthetic polymeric coating to at least one leaflet of an artificial heart valve. The synthetic polymeric coating is formed from one or more monomers, wherein at least one monomer includes a zwitterionic pendant group.

In Example 33, the method of example 32, wherein applying a synthetic polymer coating includes using one of dip coating, roll coating, spray coating, flow coating and electrostatic spraying.

In Example 34, the method of example 32, wherein applying a synthetic polymer coating includes applying a polymer brush to the surface of the leaflet.

In Example 35, the method of example 32, wherein applying a synthetic polymer coating surface includes modifying a base polymer of the leaflet by reacting a trimethoxysilane functionalized zwitterionic molecule with functional groups on a leaflet surface.

The details of one or more embodiments of devices, systems, and methods provided herein are set forth in the accompanying drawings and the description below. Other features, objects, and advantages will be apparent from the description and drawings, and from the claims.

BRIEF DESCRIPTION OF THE DRAWINGS

Like reference symbols in the various drawings indicate like elements.

DETAILED DESCRIPTION

Figure 1:
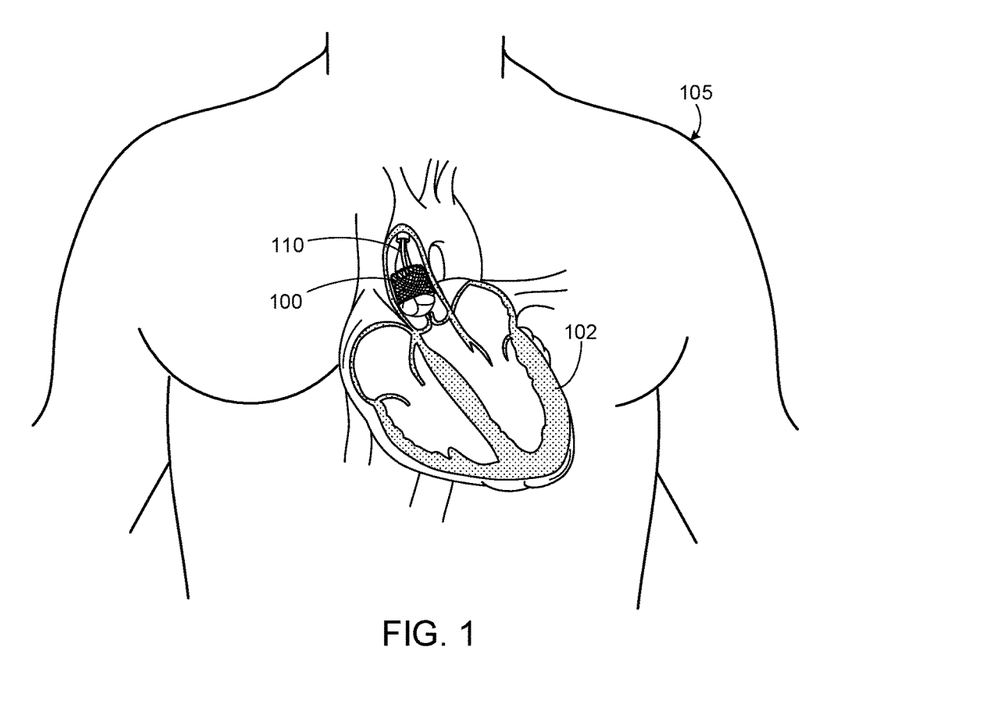
FIG. 1 is an illustration of an exemplary prosthetic heart valve provided herein within a human anatomy.

FIG. 1 shows an illustration of a prosthetic heart valve 100 provided herein within the heart 102 of a human body 105. The human body 105 has four heart valves: a pulmonary valve, a tricuspid valve, an aortic valve and a mitral valve. The purpose of the heart valves is to allow blood to flow through the heart and from the heart into the major blood vessels connected to the heart, such as the aorta and pulmonary artery. Prosthetic heart valve 100 of FIG. 1 is an aortic prosthetic heart valve that can be delivered using a transcatheter aortic valve replacement (TAVR) procedure (which is also described as percutaneous aortic valve replacement (PAVR) or transcatheter aortic valve implantation (TAVI)), which involves the use of a deployment (which can also be referred to as a delivery catheter or delivery system) placed through blood vessels from a femoral, subclavian, or direct aortic incision. Deployment device 110 can deliver prosthetic heart valve 100 to the desired location within the anatomy, and release implantable heart valve 100 at an implantation site. Although FIG. 1 shows an aortic prosthetic heart valve, it should be appreciated that prosthetic heart valve 100 can be another type of heart valve (e.g., a mitral valve or a tricuspid valve) in some cases.

Figure 2:
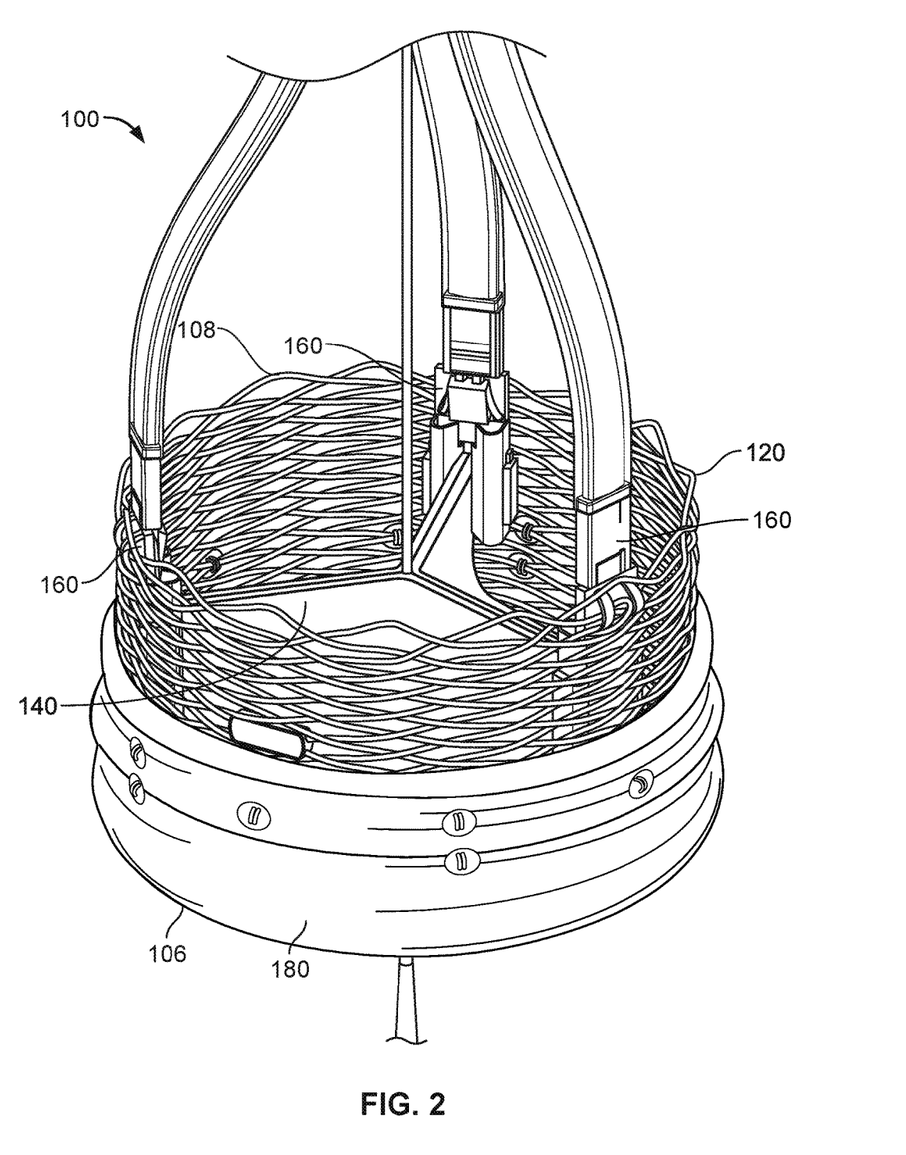
FIG. 2 is an enlarged view of the prosthetic heart valve of FIG. 1.

FIG. 2 provides a close up view of the prosthetic heart valve 100 of FIG. 1 having inflow end 106 and an outlet end 108. Prosthetic heart valve 100 has a substantially tubular body 120, a plurality of leaflets 140, anchor elements 160 and a tubular seal 180. The tubular body 120 can be a radially expandable member, e.g. annular frame or stent, having an annular cavity. As shown in FIG. 2, the heart valve 100 can have three heart valve leaflets 140 coupled to the tubular body 120 within the annular cavity. Each leaflet 140 can be secured to an adjacent leaflet 140 and to the expanding tubular body by stitches. Three anchor elements 160 positioned within the annular cavity of the tubular body can each secure the heart valve leaflets 140 to the tubular body 120. Each anchor elements 160 can be coupled to the tubular body 120 with an anchoring element 160 and also be coupled to the leaflets 140 with a clamping element. The tubular seal 180 can be disposed about at least a portion of the tubular body 120. In particular, the tubular seal 180 can have an inflow end portion 106 secured to bottom edges of the plurality of leaflets 140 and have an outflow end portion 108 disposed about an outer surface of the tubular body 120 to restrict blood flow around the leaflets 140.

In use, prosthetic heart valve 100 is implanted (e.g., surgically or through transcatheter delivery) in a mammalian heart. The edge portions of the polymeric leaflets 140 move into coaptation with one another in a closed position to substantially restrict fluid from flowing past prosthetic heart valve 100 in a closed position. The edge portions of the leaflets 140 move away from one another to an open position permitting fluid to flow past prosthetic heart valve 100. Movement of the leaflets 140 between the closed and open positions can substantially approximate the hemodynamic performance of a healthy natural valve.

Prosthetic heart valve 100 can be made of various materials. In some cases, at least of portion of the prosthetic heart valve, for example, the leaflets 140 or a portion of the tubular body 120, can be made of various synthetic materials. In some cases, the prosthetic heart valve 100 can be entirely made of synthetic materials. The synthetic materials of the prosthetic heart valve 100 can include polymeric materials, metals, ceramics, and combinations thereof. In some cases, synthetic materials of the prosthetic heart valve 100 can include a composite material composed of at least two constituent materials with different physical and/or chemical properties.

Figure 3:
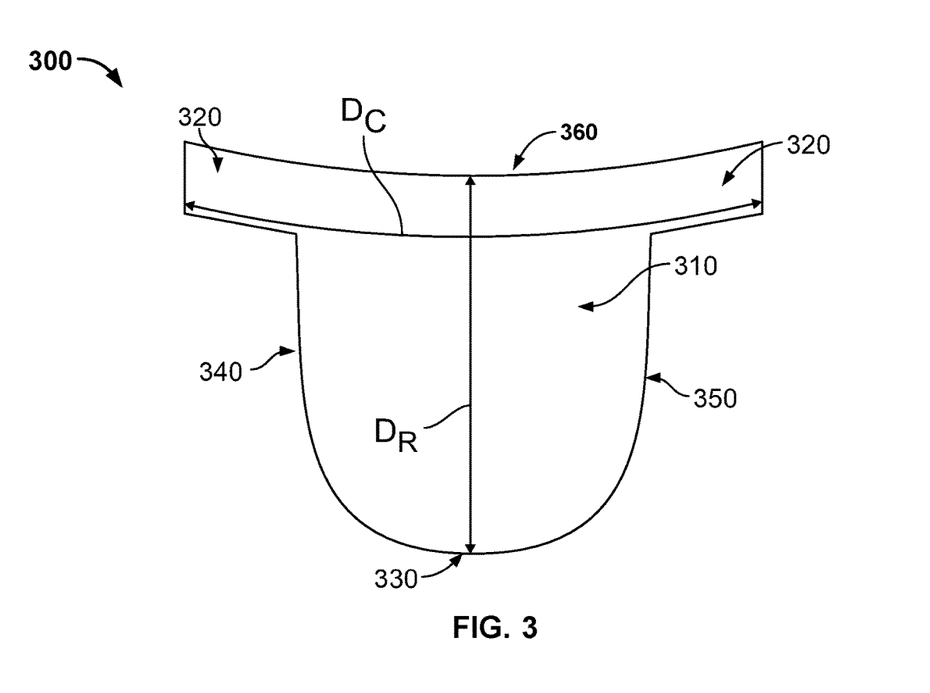
FIG. 3 is a prosthetic heart valve leaflet provided herein.

FIG. 3 shows an example of a prosthetic heart valve leaflet 300 described herein. As shown, leaflet 300 can include a body portion 310 (which can also be described as the belly region of the leaflet) and two sleeve portions 320 that extend outwardly from the body portion 310. In some cases, the body portion 310 has a bottom edge 330, a first side edge 340, a second side edge 350, and a free edge 360. Leaflet 300 further includes a front side (i.e., the side that blood flows toward), a back side (i.e., the side that blood flows away from).

As the prosthetic heart valve opens and closes, each leaflet 300 flexes between an open and a closed configuration. Tensile and flexural strain on each leaflet 300 can change depending on its configuration. As such, the leaflet 300 can elongate in various directions as the valve opens and closes. For instance, leaflet 300 can elongate in a radial direction $D_R$ and a circumferential direction $D_C$ along the body portion 310 and/or the sleeve portions 320. As shown in FIG. 3, the radial direction $D_R$ extends from the free edge 360 to the bottom edge 330 of the leaflet. A circumferential direction $D_C$ extends in a direction that is generally orthogonal to the radial direction $D_R$. In some cases, the leaflet 300 can elongate in a direction having an angle that is oblique relative to the radial and circumferential directions.

In some cases, each leaflet 300 can be made of a base polymer and can optionally include a polymer coating disposed over the base polymer. In some cases, the base polymer includes an elastic polymer. Suitable base polymer materials include, but are not limited to, homopolymers, copolymers and terpolymers of various polyurethanes (such as polyether, polyester and polyisobutylene polyurethanes (PIB-PUR)). In some embodiments, the polymer base can be formed from block polymers such as, for example, a poly(styrene-isobutylene-styrene) (SIBS) tri-block polymers. Other suitable materials include, but are not limited to, polyesters, polypropylenes, polyethylenes, polyamides, nylons and combinations thereof. Although materials described herein are directed to the leaflets 300, it should be appreciated that other components of the prosthetic heart valve can be constructed of the same materials, if desired. In some cases, for example, the prosthetic heart valve can include an expandable tubular body, e.g., the tubular body of FIG. 1, composed of a polymer layer that is the same polymer as the base polymer of the leaflets 300.

In some cases, the base polymer includes a polymer having a zwitterionic pendant group. In some cases, the polymer coating can include a zwitterionic pendant group (also described as a side group) and one or more monomers, wherein at least one monomer includes a zwitterionic group (which can also be described as a zwitterionic pendent group, a zwitterionic species or a zwitterionic compound).

A zwitterionic group, or a zwitterion (also described as a dipolar ion or an inner salt), is a neutrally charged compound, or molecule, having both a negatively charged ion and a positively charged ion. For example, as shown in Formula 1, an amino acid is a zwitterionic group since the acid has both a positively charged amino end group and a negatively charged carboxylic end group. The negatively charged ion and the positively charged ion of the zwitterionic group together creates a high polar environment.

Formula 1. Amino Acid

Zwitterions are highly hydrophilic molecules, and are sometimes described as superhydrophilic molecules. Superhydrophilicity can be a term that generally means highly hydrophilic. But in some cases, superhydrophilicity can be associated with a material that exhibits no contact angle when placed in contact with a water droplet because of its exceptionally strong affinity for water.

In some cases, a synthetic leaflet 300 can be constructed of a base polymer that includes at least one zwitterionic polymer. In some cases, a synthetic leaflet 300 can be constructed of a non-zwitterionic polymer that is subsequently coated with a zwitterionic polymer. Zwitterionic polymers can be composed of monomer units having zwitterionic side groups. The resulting polymer has zwitterionic pendant groups, which are zwitterion groups that are present in at least one repeating monomer unit of a polymer and attached to the backbone of a polymer. In some cases, a zwitterionic group could also be partially in the backbone of a polymer, e.g. R—N+(Me))-CH2SO3+)-R' with R,R' representing portions of a polymer backbone.

The zwitterionic monomers can be derived from zwitterionic species with proton doning end groups (i.e. proton donors) or accepting end groups (i.e. proton acceptors) which are functionalized with polymerizable olefinic groups. In some cases, the proton doning end groups can be hydroxyl moieties. In some cases, proton accepting end groups can be amino moieties. In some cases, suitable polymerizable olefinic groups can include, but are not limited to, acrylate, methacrylate, acrylamide and/or methacrylamide species. Once the zwitterionic monomers have been polymerized, the monomers form polymeric chains with zwitterionic pendant groups. A suitable zwitterionic monomer includes, but is not limited to, for example, carboxybetaine methacrylamide (CBMAA) as shown in Formula 2.

Formula 2. Carboxybetaine Methacrylamide (CBMAA)

In some cases, a material can have a polymer coating that includes polymerized units of a monomer including a zwitterionic group when the polymer coating is exposed to an aqueous environment, in particular blood, at a pH of about 7.4. In some cases, some of the zwitterionic groups (COO—) may be deprotonated only partially when exposed to a pH of blood, e.g., about a pH of 7.4, or between a pH of about 7 to 8. In some cases, a zwitterionic group of a monomer can be formed by a carboxylic acid group, a sulfonic acid group, or a phosphoric acid group. In some cases, a monomer can include a zwitterionic group composed of an acrylate, a methacrylate, an acrylamide, or a methacrylamide. In some cases, a cation of a zwitterionic group can be formed by an (cyclo)aliphatic or aromatic amine, an amidine, or a guanidine. In some cases, a cation of a zwitterionic group can be a quaternary amine.

In some cases, a cation and an anion of a zwitterionic group can be part of the same pendant group of the monomer unit. In some cases, the pendant group has the structure formula: X—(CH2)n-N+R2-(CH2)m-Y or X—(CH2)n-O—P(O—)—(CH2)m-Z, wherein:

X is the point of covalent attachment to the repeat unit of the monomer;

each R is independently selected from C1- to C4-alkyl, in particular methyl;

n and m are each integers between 1 and 8;

Y is a anionic group selected from COO—, SO3-, O—SO3-, O—PO3-, and PO3-; and Z is a cationic group derived from a (cyclo)aliphatic or aromatic amine, an amidine, a guanidine, or a quaternary amine, in particular NR'3+, wherein each R' is independently selected from C1- to C4-alkyl, in particular methyl.

As shown in Formulas 4-6, other suitable monomers can include betaine monomers carboxybetaine (Formula 3), phosphobetaine (Formula 4) and sulfobetaine N,N'-dimethyl (methacryloylethyl)ammonium propanesulfonate (Formula 5), also known as sulfobetaine methacrylate. (SBMA).

Formula 3

Formula 4

Formula 5

Other suitable zwitterionic monomers that may be used to form zwitterionic polymers that can be applied to coatings and materials used for forming synthetic heart valves bodies and/or leaflets 300 include, but are not limited to, 2-Methacryloyloxyethyl phosphorylcholine shown in Formula 7, [3-(Methacryloylamino)propyl]dimethyl(3-sulfopropyl)ammonium hydroxide inner salt (also known as 3-(dimethyl{3-[(2-methylacryloyl)amino]propyl}ammonio)propane-1-sulfonate) shown in Formula 8, [2-(Methacryloyloxy)ethyl]dimethyl-(3-sulfopropyl)ammonium hydroxide (also known as dimethyl-[2-(2-methylprop-2-enoyloxy)ethyl]-(3-sulfopropyl)azanium), and any derivatives, analogs, homologues, congeners, salts, copolymers and combinations thereof.

Formula 7. 2-Methacryloyloxyethyl phosphorylcholine

Formula 8: 3-(dimethyl{3-[(2-methylacryloyl)amino]propyl}ammonio)propane-1-sulfonate Zwitterionic monomers may be used to prepare homopolymer chains, or in combination with other monomers or to create random-, block-, or alternating-copolymer systems. In some cases, zwitterionic monomers can be used to prepare to linear architectures, combs, stars, brushes, hyperbranched/arborescent, and crosslinked gel systems may also be used. The length of the graft and density of the graft chains on the surface can be optimized to enhance anti-calcification effects.

Incorporating zwitterionic polymers in a prosthetic heart valve can provide the benefit of minimizing or preventing biological responses normally caused by synthetic materials implanted in a body. In some cases, for example, zwitterionic polymers can minimize or prevent calcification in an implanted artificial heart valve. Other benefits of using a zwitterionic polymeric surface include increasing the hydrophilicity, nonspecific protein adsorption resistance and/or platelet adhesion resistance of synthetic surfaces. Because zwitterionic polymers are characterized as having super hydrophilic properties, these polymers can create a water-saturated surface, or layer, on synthetic materials. Water-saturated surfaces generally inhibit protein adsorption, which can lead to subsequent calcification, thrombus formation, microbiological organism adsorption, cell attachment and/or biofouling.

Synthetic leaflets 300 can optionally be made from or coated with a zwitterionic copolymer. A zwitterionic copolymer can be composed of at least two distinct monomer units. In some cases, each monomer unit can have a different zwitterionic group. A zwitterionic copolymer, in some cases, can be composed of monomer units having zwitterionic groups and monomers units having non-zwitterionic groups. In some cases, a zwitterionic copolymer can be formed from vinyl monomers including, but not limited to, styrenics, vinyl pyridines, and vinyl imidazoles. In some cases, a zwitterionic polymer or copolymer can include sulfobetaines or phosphobetaines. In some cases, zwitterionic copolymer can include non-zwitterionic monomers having different hydrophilicities or hydrophobicity than the zwitterionic monomers. A zwitterionic copolymer may provide a synthetic leaflet with chemical, physical, and mechanical properties of two or more materials.

In some cases, zwitterionic copolymers can be formed by combining a zwitterionic polymer with another polymer, such as a non-zwitterionic polymer. Various types of polymers can be combined with a zwitterionic polymer to create a zwitterionic copolymer. In some cases, zwitterionic polymers can be combined with polyethylene glycol (PEG) to create copolymers having superhydrophilic properties, for example. Zwitterionic copolymers, such as block copolymers and random copolymers, branched, end-capped, glycol or a plural polymer end cap, can be envisioned by one skilled in the art for producing leaflet materials.

Synthetic leaflets 300 described herein can include a plurality of fibers. In some cases, the plurality of fibers can be embedded in the base polymer. In some cases, the plurality of fibers are each oriented in an extending direction and each include a plurality of undulations orthogonal to the extending direction, wherein the plurality of undulations of the plurality of fibers are adapted to provide each leaflet 300 with multi-stage elastic properties.

Figure 4:
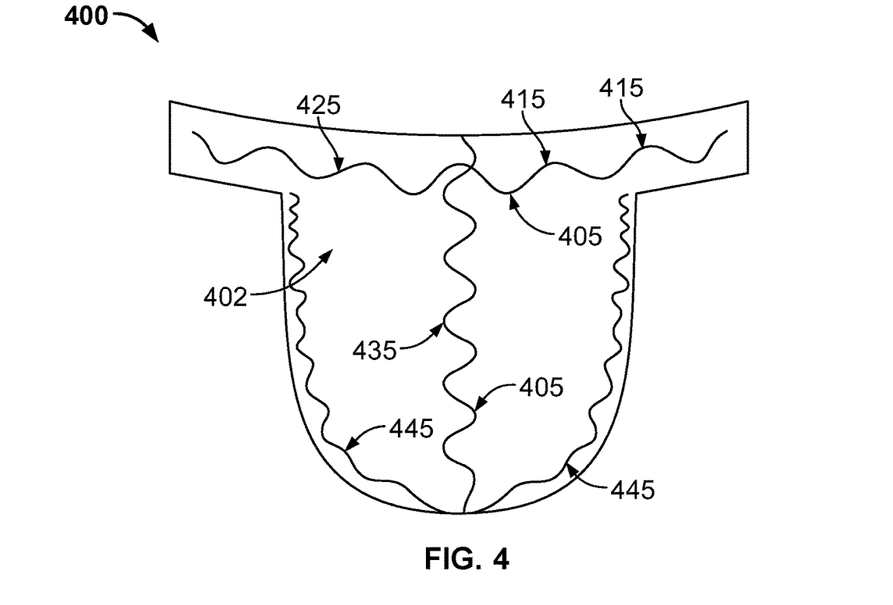
FIG. 4 shows fiber configurations of an exemplary leaflet provided herein.

FIG. 4 shows another exemplary leaflet 400 of a prosthetic heart tissue valve described herein. Leaflet 400 can be made of a material that includes a plurality of fibers 405 embedded in a base polymer 402 that is composed of at least one zwitterionic polymer. Each fiber 405 can have an extending direction and a plurality of undulations 415 orthogonal to the extending direction. As shown in FIG. 4, at least a portion of the plurality of fibers 405 extends in a circumferential direction, a radial direction, and a direction along at least a portion of an edge profile of the leaflet 400. Leaflet 400 of FIG. 4 has circumferentially-directed fibers 425 that extend from one side edge to the opposite side edge of a sleeve portion and radially-directed fibers 435 that extend from a free edge to a bottom edge of the leaflet 400. Furthermore, as shown, leaflet 400 has at least one curvilinear fiber 445 that begins at one side edge of a leaflet belly region and ends at an opposite side edge, extending along a U-shape contour therebetween. In some cases, leaflet 400 can have curvilinear fibers 445 in the body portion and/or sleeve portion. In some cases, the curvilinear fibers 445 are shaped similar to an outline edge of the leaflet 400, for example, fibers extending along the U-shape contour of the leaflet 400. In some cases, the curvilinear fibers 445 can be shaped to a form or contour that provides a desired elasticity to a particular area of the leaflet 400.

Fibers can have diameters or average diameters of at least 1 micron (or 0.00004 inches). Fibers can be, in some cases, in the range of about 1 micron to about 100 microns (or about 0.00004 inches to about 0.004 inches), including all ranges and values therebetween. In some cases, for example, suitable fiber diameter sizes can include ranges of about 1 micron to 5 microns (or about 0.00004 inches to about 0.0002 inches), 5 microns to 10 microns (or 0.0002 inches to about 0.0004 inches), 10 microns to 20 microns (or 0.0004 inches to about 0.0008 inches), 20 microns to 50 microns (or 0.0008 inches to about 0.0020 inches), and 50 microns to 100 microns (or 0.002 inches to about 0.004 inches).). In some cases, fibers can have diameters in the range of about 1 microns to about 10 microns (or 0.0004 inches to about 0.0020 inches), including all ranges and values therebetween. In some cases, the fiber made from polymers can range from about 5 microns to about 100 microns (or 0.00002 inches to about 0.0040 inches), from about 10 microns to about 75 microns (or 0.0004 inches to about 0.003 inches), from about 10 micron to about 50 microns (or 0.0004 inches to about 0.0020 inches), from about 20 microns to about 100 microns (or 0.0008 inches to about 0.0040 inches), from about 25 microns to about 200 microns (or 0.001 inches to about 0.008 inches), or from about 20 microns to about 50 microns (or 0.0008 inches to about 0.002 inches). In some cases, fibers 505, such as LCP fibers, can range from 0.5 microns (or 500 nanometers) to 5 microns (or about 0.00002 inches to about 0.00020 inches). In some cases, fibers can have diameters or average diameters less than 1 micron, or 1000 nanometers (nm) (or 0.00004 inches).

Fibers of the leaflets described herein can be made of various materials suitable for medical devices and/or implants. The fibers can be made of various biostable and/or biocompatible materials. A biostable material is a material that is resistant to degradation during the use life of a medical device and is not associated with carcinogenicity issues. A biocompatible material is a synthetic or natural material that is not harmful to living tissue. In general, fibers described herein can be composed of polymers, metals (e.g., titanium, stainless steel, tantalum), ceramics (fiberglass, acrylics), or combinations thereof. In some case, fibers are made of thermoplastic polymers, thermoset polymers or combinations thereof. Fibers provided herein can be made of various polymeric materials, such as fluoropolymers, polyurethanes or block copolymers. Suitable polymers for fibers provided herein can be formed from fluoropolymers including, but not limited to, for example, polytetrafluoroethylene (PTFE), polyvinylidene fluoride (PVDF) (e.g. Kynar™ and Solef™), poly(vinylidene fluoride-co-hexafluoropropene) (PVDF-HFP) and combinations thereof. Other suitable fiber polymers can include urethane-based polymers such as polyurethanes, polyurethane elastomers (e.g. Pellethane), polyether-based polyurethanes (e.g. Tecothane), polycarbonate-based polyurethanes (e.g. Bionate and Chronoflex) and combinations thereof. In some cases, other examples of suitable polymer materials for fibers include, but are not limited to, polycarbonates, polyethers, polyesters such as polyethylene terephthalate (PET), polyethylenes, polypropylenes, polyamides (e.g., Kelvar®, Pebax®, nylon 6 and nylon 12), polyetheretherketones (PEEK), polysulfones, polyvinyl alcohols, polyetherimides, polyimide (PI), polybenoxazole (PBO), polybenzothiazole (PBT), polybenzimidazole (PBI), poly-N-phenylbenzimidazole (PPBI), polyphenylquinoxaline (PPG), poly(p-phenylene terephthalamide) (PPTA), polysulfone, naphtalate based polymer fibers such as polybuthylenenaphtalate (PBN) and polyethylenenaphtalate (PEN), polyhydroquinone-diimidazopyridine (PIPD or also known as M5 fibers) and combinations thereof. In some cases, fibers are formed from block copolymers such as, for example, a poly(styrene-isobutylene-styrene) (SIBS) tri-block polymer and a polyisobutylene urethane copolymer (PIB-PUR).

Fibers can, in some cases, be made of a liquid crystalline polymer (LCP). LCPs are a special class of aromatic polyester or polyamide copolymers that have semi-crystalline properties due to regions of highly ordered crystalline structures formed therein. LCPs are materials that are generally chemically inert and have a high creep resistance, a high modulus and a high tensile strength. Suitable fiber materials made of LCPs include, but are not limited to, thermotropic polyesters such as Vectran®, poly(p-phenylene terephthalamide) (PPTA), poly(phenylene benzobisoxazole) (PBO), and combinations thereof. Other suitable LCPs can include poly(p-phenylene terephthalamide) such as Kevlar®, Vectran®, Poly(m-phenylene isophthalamide) such as Nomex® and Teijinconex®, Herachron®, Technora®, Twaron®, and Zylon®. In some cases, other high performance fibers can utilized, such as gel-spun ultra-high molecular weight polyethylene (Dyneema® and Spectra®). Benefits of using LCPs include providing leaflets with optionally thinner and smaller dimensions, e.g., thickness or diameter, without compromising mechanical properties of the leaflet, such as tensile strength, or performance characteristics such as robustness and durability. In some cases, diameters of LCP fibers can be as small as 0.5 micrometers (or μm). In some cases, thicknesses of a leaflet composed of LCP fibers can range from about 50 μm to about 100 μm.

In some cases, individual fibers can be encapsulated within a jacket (e.g., a polymer jacket) to promote bonding between the fibers and the polymer matrix. In some cases, for example, the leaflet can include LCP fibers that have been encapsulated within a polymer jacket.

In some cases, the synthetic leaflet 400 can be made of a non-zwitterionic base polymer that is surface modified to include a zwitterionic pendant group. More specifically, in some cases, zwitterionic polymers can be grafted onto the base polymer surface using surface-initiated atom transfer radical polymerization (ATRP). ATRP is a method of polymerization that forms carbon bonds using a transition metal catalyst, such as copper, iron, molybdenum, osmium and ruthenium. The transition metal catalyst reacts with an alkyl halide initiator, such as copper chloride (CuCl) or copper bromide (CuBr), to form a transition metal complex. The transition metal complex then activates a dormant species that produces a propagating radical. In some cases, modification of the surface of a non-zwitterionic base polymer is beneficial because the desirable bulk properties of the non-zwitterionic base polymer can be maintained, if desired. In some cases, the desirable bulk properties of the non-zwitterionic base polymer can be maintained by modifying a surface layer having a thickness of about 50 to about 1000 nanometers. For example, if the base polymer is a flexible polyurethane, desirable properties of that polyurethane are maintained by using a surface modification method to apply zwitterionic polymers. Accordingly, the benefits of using zwitterionic materials, such as improved biocompatibility and protein resistance as well as reduced thrombotic responses calcification, can be realized in a polyurethane base polymer.

Figure 5:
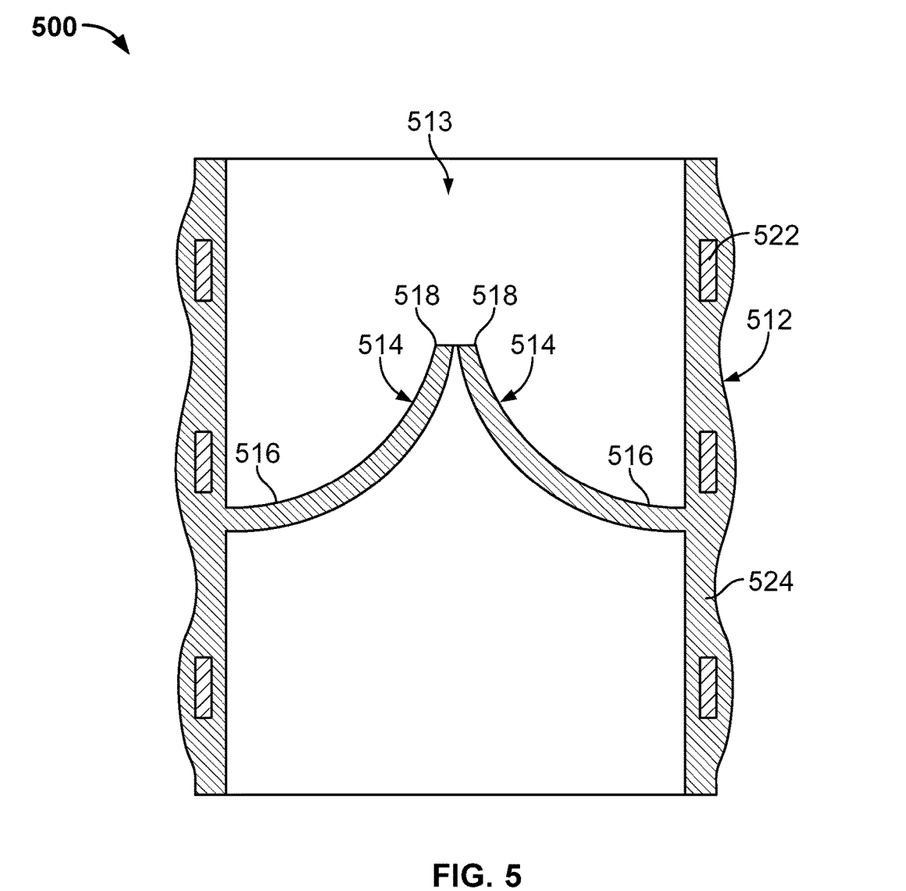
FIG. 5 is a side view of another exemplary prosthetic heart valve provided herein.

FIG. 5 provides another embodiment of an artificial heart valve 800. Prosthetic heart valve 500 includes a base 512 defining a substantially cylindrical passage 513 and a plurality of polymeric leaflets 514 disposed along the substantially cylindrical passage 513. Each polymeric leaflet 514 includes a respective root portion 516 coupled to base 512 and a respective edge portion 518 movable relative to the root portion 516 to coapt with the edge portions of the other polymeric leaflets along a coaptation region. In some cases, the base 512 and/or the leaflets 514 can be made from or coated with a zwitterionic polymer.

Base 512 includes a frame 522 disposed in a polymer layer 524 that can be optionally made from or coated with a zwitterionic polymer. Polymer layer 524 secures respective root portions 516 of polymeric leaflets 514 to the base 512. Polymer layer 524 can form a substantially continuous surface with respective root portions 516 of polymeric leaflets 514. This can reduce the likelihood of stress concentrations at the junction of respective root portions 516 and base 512. Additionally or alternatively, polymer layer 524 can be disposed between each of polymeric leaflets 514 and frame 522 such that polymer layer 524 protects polymeric leaflets 514 from inadvertent contact with frame 522 (e.g., as can occur through eccentric deformation of prosthetic heart valve 500 on a calcium deposit present at the implantation site).

In some cases, frame 522 is substantially cylindrical such that the outer surface of the base 512 is substantially cylindrical and the polymer layer 524 disposed on the frame 522 forms the substantially cylindrical passage 513. In some cases, frame 522 is completely disposed in the polymer layer 524, with the polymer layer 524 forming a contoured outer surface of the valve 500. In some cases, the frame 522 is partially disposed in the polymer layer 524. In some cases, the polymer layer 524 is applied to the frame 522 to form a substantially smooth inner and/or outer surface of the valve 500.

Zwitterionic polymers used for heart valve leaflet fabrication can be formed using various methods described herein. Specifically, in some cases, at least one end group of the zwitterionic polymers can be functionalized and attached, or linked, to another synthetic material. Polymerization reactions that form and attach zwitterionic polymers to a surface can be initiated using a photo, thermal and/or chemical initiator. In some cases, diallyl ammonium compounds can be used as a crosslinking agent, as described in U.S. Application 20080045420, which is incorporated by reference herein in its entirety. Polymerization reactions can be facilitated by using a traditional end-linking polymerization synthesis method, or by using an on-surface synthesis method. As implied by the name, on-surface synthesis is a type of synthesis in which covalent bonds are formed between molecular units directly on a surface. As such, on-surface synthesis can create surface modifications that attach zwitterionic polymers directly to the surface. On-surface synthesis can have the benefit of producing reactions that might be otherwise difficult to achieve when using the traditional method.

Various methods can be used to include zwitterionic polymers provided herein into a device component or attach to a surface. Suitable methods of include, but are not limited to, compression molding, extrusion, solvent casting, injection molding, electrospinning, force spinning, melt-blowing, and combinations thereof. Examples of additional methods for partially or fully constructing a leaflet part include, but are not limited to, dip coating, roll coating, spray coating, flow coating, electrostatic spraying, plasma spraying, spin coating, curtain coating, silkscreen coating, and combinations thereof.

Compression molding can be used to produce sheets or molded parts composed of a leaflet material. The compression molding process is a process of forming a part by placing a preformed polymeric material, such as a preformed thermoset compound, directly into a heated metallic mold. The preformed thermoset compound conforms to the shape of the mold as it becomes pliable and compressed by the heated mold. In some cases, a leaflet material can be made by inserting one or more preformed compounds and/or one or more fibrous matrixes into a compression mold.

Extrusion and injection molding can be used to form at least a portion of a part composed of zwitterionic polymers, in some cases. Extrusion is a process of forming parts with a fixed cross-section profile by pushing or pulling a material through a die having a desired cross-section. Injection molding is a process that feds one or more heated materials into a mold cavity and cools the materials in the shape of the cavity. Either of these processes can be used to make a leaflet base polymer before or after incorporating a layer of fibers.

Solvent casting is another process that can be used to form a component including zwitterionic polymers. This process involves dissolving a polymer material in an organic solvent, casting the solution in a mold and drying the solvent to create a final structure.

Various methods can be employed to form fibers of a leaflet that includes zwitterionic polymers. Examples of some suitable methods can include, but are not limited to, electrospinning, force spinning and melt-blowing processes. Electrospinning, force spinning and melt-blowing processes are exemplary processes that can be used to form fibers. Electrospinning is a process that uses electrical charge to create fibers from a liquid while force spinning is a process that uses centrifugal force to create fibers. Melt-blowing is a process in which a molten thermoplastic resin is extruded through a die and then stretched and cooled with high-velocity air to form long, fine fibers. Both electrospinning and melt-blowing processes can be used to form fibers into a woven a non-woven fibrous matrix. In some cases, multiple fiber materials can be formed simultaneously by one or more apparatuses.

In some cases, surface modifications of a base polymer of a leaflet can occur by reacting a trimethoxysilane functionalized zwitterionic molecule with functional groups on a surface. This surface functionalization imparts superhydrophilic properties to the surface that can provide the benefits of preventing adsorption of lipids, proteins, bacteria, cells, etc. In some cases, silane ortho esters (and silane ortho halides) can be used for modification of surfaces with metal oxides or proton donating functional groups, such as carboxic acids, alcohols, amines, or amides.

In some cases, zwitterionic polymers can be attached to the surface using polymer brushes. As described by U.S. Patent Application No. 2014/0018440, "polymer brushes," as the name suggests, contain polymer chains, one end of which is directly or indirectly tethered to a surface and another end of which is free to extend from the surface, somewhat analogous to the bristles of a brush. There a variety of ways of applying a polymer brush to surface modify a base polymer, such as those described in U.S. Patent Application No. 2014/0018440, which is hereby incorporated by reference in its entirety. Accordingly, in some cases, a base polymer can be modified with zwitterionic polymers by applying polymer brushes to the surface of the base polymer.

A number of embodiments of devices, systems, and methods have been described herein. Nevertheless, it will be understood that various modifications may be made without departing from the spirit and scope of the subject matter described herein. Accordingly, other embodiments are within the scope of the following claims.

What is claimed is:

1. A prosthetic heart valve comprising
   a plurality of synthetic polymeric leaflets, each leaflet having a base polymer and a polymer coating disposed over the base polymer,
   wherein the polymer coating comprises a trimethoxysilane functionalized polymer comprising zwitterionic pendant groups, wherein each zwitterionic pendant group comprises an anionic group and a cationic group.

2. The prosthetic heart valve of claim 1, wherein the anionic group of the zwitterionic pendant group is formed by a phosphoric acid group.

3. The prosthetic heart valve of claim 1, wherein the cationic group of the zwitterionic pendant group is formed by an (cyclo)aliphatic or aromatic amine, an amidine, or a guanidine; or is a quaternary amine.

4. The prosthetic heart valve of claim 1, wherein the polymer coating consists essentially of the polymer comprising zwitterionic pendant groups.

5. The prosthetic heart valve of claim 1, wherein the cationic group is a quaternary amine.

6. The prosthetic heart valve of claim 1, wherein the pendant group has the structure X—$(CH_2)_n$—O—Y—$(CH_2)_m$—Z, wherein:
   X is the point of covalent attachment to the repeat unit of the monomer;
   each R is independently selected from C1- to C4-alkyl;
   n and m are each integers between 1 and 8;
   Y is either $P(O^-)$ or $PO_3^-$; and
   Z is a cationic group derived from a (cyclo)aliphatic or aromatic amine, an amidine, a guanidine, or a quaternary amine, $NR'_3{}^+$, wherein each R' is independently selected from C1- to C4-alkyl.

7. The prosthetic heart valve of claim 1, wherein the polymer of the polymer coating is the reaction product of one or more monomer species having a structure selected from the group consisting of:

Formula 5

8. The prosthetic heart valve of claim 1, wherein the polymer comprising a zwitterionic pendant group is the reaction product of monomers including one or more of an acrylate, a methacrylate, an acrylamide, or a methacrylamide.

9. The prosthetic heart valve of claim 1, wherein each leaflet comprises a plurality of fibers.

10. The prosthetic heart valve of claim 9, wherein the plurality of fibers are embedded in the base polymer, each fiber being oriented in an extending direction and comprising a plurality of undulations.

11. The prosthetic heart valve of claim 1, wherein the prosthetic heart valve comprises an expandable tubular body, wherein the expandable tubular body comprises a polymer layer comprising the same polymer as the base polymer of the plurality of leaflets.

12. The prosthetic heart valve of claim 1, wherein the base polymer comprises polyisobutylene polyurethanes (PIB-PUR).

13. A prosthetic heart valve comprising
a plurality of synthetic polymeric leaflets, each leaflet having a base polymer and a polymer coating disposed over the base polymer,
wherein the polymer coating comprises a trimethoxysilane functionalized polymer that is the reaction product of one or more monomers comprising zwitterionic pendant groups and one or more monomers comprising non-zwitterionic pendent groups.

14. The prosthetic heart valve of claim 13, wherein the polymer of the polymer coating is the reaction product of a monomer comprising zwitterionic pendant groups having a structure selected from the group consisting of:

Formula 5

; and

15. A prosthetic heart valve comprising
a plurality of synthetic polymeric leaflets, each leaflet having a base polymer and a polymer coating disposed over the base polymer;
wherein the polymer coating comprises a polymer comprising zwitterionic pendant groups, wherein each zwitterionic pendant group comprises an anionic group and a cationic group; and
wherein the polymer of the polymer coating comprises the reaction product of one or more monomer species having a structure selected from the group consisting of:

; and

16. The prosthetic heart valve of claim 15, wherein the polymer of the polymer coating is functionalized with a trimethoxysilane.

* * * * *